US009854979B2

(12) United States Patent
Smith et al.

(10) Patent No.: US 9,854,979 B2
(45) Date of Patent: Jan. 2, 2018

(54) CHRONIC TOTAL OCCLUSION CROSSING DEVICES WITH IMAGING

(71) Applicant: AVINGER, INC., Redwood City, CA (US)

(72) Inventors: Peter H. Smith, Pacifica, CA (US); Manish Kankaria, Fremont, CA (US); Priyanshu Gupta, Palo Alto, CA (US); Nicholas J. Spinelli, San Carlos, CA (US); Charles W. McNall, Cottonwood Heights, UT (US)

(73) Assignee: Avinger, Inc., Redwood City, CA (US)

( * ) Notice: Subject to any disclaimer, the term of this patent is extended or adjusted under 35 U.S.C. 154(b) by 46 days.

(21) Appl. No.: 14/776,750

(22) PCT Filed: Mar. 15, 2013

(86) PCT No.: PCT/US2013/032679
§ 371 (c)(1),
(2) Date: Sep. 15, 2015

(87) PCT Pub. No.: WO2014/143064
PCT Pub. Date: Sep. 18, 2014

(65) Prior Publication Data
US 2016/0029902 A1 Feb. 4, 2016

(51) Int. Cl.
*A61B 6/00* (2006.01)
*A61B 5/02* (2006.01)
(Continued)

(52) U.S. Cl.
CPC ........ *A61B 5/02007* (2013.01); *A61B 1/0055* (2013.01); *A61B 1/04* (2013.01);
(Continued)

(58) Field of Classification Search
CPC ..... A61B 5/02007; A61B 1/0055; A61B 1/04; A61B 1/07; A61B 1/3137; A61B 5/0066;
(Continued)

(56) References Cited

U.S. PATENT DOCUMENTS 4,178,935 A 12/1979 Gekhaman et al.
4,527,553 A 7/1985 Upsher
(Continued)

FOREIGN PATENT DOCUMENTS

CN 1875242 A 12/2006
CN 1947652 A 4/2007
(Continued)

OTHER PUBLICATIONS

Simpson et al.; U.S. Appl. No. 14/899,877 entitled "Occusion sheath for imaging catheter," filed Dec. 18, 2015.
(Continued)

*Primary Examiner* — Robert N Wieland
(74) *Attorney, Agent, or Firm* — Shay Glenn LLP

(57) ABSTRACT

An imaging device includes a hollow flexible shaft having a central longitudinal axis and an imaging window therein. An optical fiber extends within the hollow flexible shaft substantially along the central axis. A distal tip of the optical fiber is attached to the hollow flexible shaft and aligned with the imaging window so as to transfer an optical coherence tomography signal through the imaging window. A handle is attached to the hollow flexible shaft configured rotate the hollow flexible shaft at speeds of greater than 1,000 rpm.

15 Claims, 13 Drawing Sheets

(51) Int. Cl.
  *A61B 5/00* (2006.01)
  *A61B 17/3207* (2006.01)
  *A61B 1/005* (2006.01)
  *A61B 1/04* (2006.01)
  *A61B 1/07* (2006.01)
  *A61B 1/313* (2006.01)
  *A61B 17/32* (2006.01)
  *A61B 17/22* (2006.01)
  *A61B 90/00* (2016.01)

(52) U.S. Cl.
  CPC .............. *A61B 1/07* (2013.01); *A61B 1/3137* (2013.01); *A61B 5/0066* (2013.01); *A61B 5/0084* (2013.01); *A61B 5/4836* (2013.01); *A61B 5/6851* (2013.01); *A61B 5/6852* (2013.01); *A61B 17/320016* (2013.01); *A61B 17/320758* (2013.01); *A61B 2017/22038* (2013.01); *A61B 2090/3618* (2016.02); *A61B 2090/3735* (2016.02)

(58) Field of Classification Search
  CPC ... A61B 5/0084; A61B 5/4836; A61B 5/6851; A61B 5/6852
  See application file for complete search history.

(56) References Cited

U.S. PATENT DOCUMENTS

| | | |
|---|---|---|
| 4,552,554 A | 11/1985 | Gould et al. |
| 4,621,353 A | 11/1986 | Hazel et al. |
| 4,639,091 A | 1/1987 | Huignard et al. |
| 4,654,024 A | 3/1987 | Crittenden et al. |
| 4,686,982 A | 8/1987 | Nash |
| 4,771,774 A | 9/1988 | Simpson et al. |
| 4,841,977 A | 6/1989 | Griffith et al. |
| 4,926,858 A | 5/1990 | Gifford, III et al. |
| 5,000,185 A | 3/1991 | Yock |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,383,460 A | 1/1995 | Jang et al. |
| 5,383,467 A | 1/1995 | Auer et al. |
| 5,429,136 A | 7/1995 | Milo et al. |
| 5,431,673 A | 7/1995 | Summers et al. |
| 5,459,570 A | 10/1995 | Swanson et al. |
| 5,465,147 A | 11/1995 | Swanson |
| 5,507,795 A | 4/1996 | Chiang et al. |
| 5,556,405 A | 9/1996 | Lary |
| 5,620,426 A | 4/1997 | Braithwaite |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,615,071 B1 | 9/2003 | Casscells, III et al. |
| 6,638,233 B2 | 10/2003 | Corvi et al. |
| 6,645,217 B1 | 11/2003 | MacKinnon et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |

(56) References Cited

U.S. PATENT DOCUMENTS

| | | |
|---|---|---|
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,313,493 B2 | 11/2012 | Fischer |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,351,757 B2 | 5/2016 | Kusleika |
| 2001/0020126 A1 | 9/2001 | Swanson et al. |
| 2002/0019644 A1 | 2/2002 | Hastings et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0158547 A1 | 10/2002 | Wood |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038173 A1 | 2/2007 | Simpson |
| 2007/0078469 A1 | 4/2007 | Soito et al. |

(56) References Cited

U.S. PATENT DOCUMENTS

| | | |
|---|---|---|
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0196926 A1 | 8/2007 | Soito et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0049225 A1 | 2/2010 | To et al. |
| 2010/0080016 A1 | 4/2010 | Fukui et al. |
| 2010/0125253 A1 | 5/2010 | Olson |
| 2010/0130996 A1 | 5/2010 | Doud et al. |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |
| 2010/0317973 A1 | 12/2010 | Nita |
| 2010/0324472 A1 | 12/2010 | Wulfman |
| 2011/0004107 A1 | 1/2011 | Rosenthal et al. |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0257478 A1 | 10/2011 | Kleiner et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1* | 12/2011 | Palme ............... A61B 17/32075 606/127 |
| 2012/0004506 A1 | 1/2012 | Tearney et al. |
| 2012/0046679 A1 | 2/2012 | Patel et al. |
| 2012/0123352 A1 | 5/2012 | Fruland et al. |
| 2012/0238869 A1 | 9/2012 | Schmitt et al. |
| 2012/0253186 A1* | 10/2012 | Simpson ........... A61B 17/32075 600/426 |
| 2012/0259337 A1 | 10/2012 | del Rio et al. |
| 2012/0289971 A1 | 11/2012 | Segermark et al. |
| 2013/0035692 A1 | 2/2013 | Sorensen et al. |
| 2013/0096589 A1 | 4/2013 | Spencer et al. |
| 2013/0123615 A1 | 5/2013 | Spencer et al. |
| 2013/0138128 A1 | 5/2013 | Patel et al. |
| 2013/0211221 A1 | 8/2013 | Sunnarborg et al. |
| 2013/0223801 A1 | 8/2013 | Bhagavatula et al. |
| 2013/0266259 A1 | 10/2013 | Bhagavatula et al. |
| 2013/0289392 A1 | 10/2013 | Patel et al. |
| 2013/0296695 A1 | 11/2013 | Spencer et al. |
| 2013/0317519 A1 | 11/2013 | Romo et al. |
| 2014/0005534 A1 | 1/2014 | He et al. |
| 2014/0128893 A1 | 5/2014 | Guggenheimer et al. |
| 2014/0213893 A1 | 7/2014 | Simpson et al. |
| 2014/0222047 A1 | 8/2014 | Vreeman |
| 2014/0371718 A1* | 12/2014 | Alvarez ............. A61M 25/0074 604/510 |
| 2015/0025310 A1 | 1/2015 | Everingham et al. |
| 2015/0099984 A1 | 4/2015 | Kankaria |
| 2015/0126856 A1 | 5/2015 | Tachibana et al. |
| 2015/0141816 A1 | 5/2015 | Gupta et al. |
| 2015/0164530 A1 | 6/2015 | Carver et al. |
| 2015/0208922 A1 | 7/2015 | Simpson et al. |
| 2015/0272615 A1 | 10/2015 | Newhauser et al. |
| 2015/0320975 A1 | 11/2015 | Simpson et al. |
| 2016/0192962 A1 | 7/2016 | Simpson et al. |
| 2016/0199092 A1 | 7/2016 | Patel et al. |

FOREIGN PATENT DOCUMENTS

| | | |
|---|---|---|
| CN | 101601581 A | 12/2009 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2353526 B1 | 9/2013 |
| JP | H06-027343 A | 2/1994 |
| JP | H07-308393 A | 11/1995 |
| JP | 2002-214127 A | 7/2002 |
| JP | 2004-509695 A | 4/2004 |
| JP | 2004-516073 | 6/2004 |
| JP | 2005-114473 A | 4/2005 |
| JP | 2005-249704 A | 9/2005 |
| JP | 2005-533533 A | 11/2005 |
| JP | 2008-175698 A | 7/2006 |
| JP | 2006-288775 A | 10/2006 |
| JP | 2006-313158 A | 11/2006 |
| JP | 2006-526790 | 11/2006 |
| JP | 2006-326157 A | 12/2006 |

(56) References Cited

FOREIGN PATENT DOCUMENTS

| | | |
|---|---|---|
| JP | 2007-83053 A | 4/2007 |
| JP | 2007-83057 A | 4/2007 |
| JP | 2007-225349 A | 9/2007 |
| JP | 2007533361 A | 11/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| JP | 2009-509690 A | 3/2009 |
| JP | 2009-66252 A | 4/2009 |
| JP | 2009-78150 A | 4/2009 |
| JP | 2010518900 A | 6/2010 |
| JP | 2012533353 A | 12/2012 |
| KR | 2007/0047221 | 5/2007 |
| RU | 2185859 C2 | 7/2002 |
| RU | 2218191 C2 | 12/2003 |
| WO | WO 91/17698 A1 | 11/1991 |
| WO | WO 99/23958 A1 | 5/1999 |
| WO | WO 00/54659 A1 | 9/2000 |
| WO | WO01/15609 A1 | 3/2001 |
| WO | WO 01/76680 A1 | 10/2001 |
| WO | WO 2006/133030 A2 | 12/2006 |
| WO | WO2008/005888 A2 | 1/2008 |
| WO | WO 2008/029506 A | 3/2008 |
| WO | WO 2008/042987 A2 | 4/2008 |
| WO | WO2008/051951 A1 | 5/2008 |
| WO | WO 2008/065600 A2 | 6/2008 |
| WO | WO 2008/086613 A1 | 7/2008 |
| WO | WO 2008/087613 A2 | 7/2008 |
| WO | WO2009/005779 A1 | 1/2009 |
| WO | WO2009/006335 A1 | 1/2009 |
| WO | WO 2009/009799 A1 | 1/2009 |
| WO | WO2009/009802 A1 | 1/2009 |
| WO | WO 2009/023635 A | 2/2009 |
| WO | WO2009/024344 A1 | 2/2009 |
| WO | WO 2009/094341 A2 | 7/2009 |
| WO | WO 2009/140617 A2 | 11/2009 |
| WO | WO2010/039464 A1 | 4/2010 |
| WO | WO2010/056771 A1 | 5/2010 |
| WO | WO 2012/061935 A1 | 5/2012 |
| WO | WO2012/166332 A1 | 12/2012 |

OTHER PUBLICATIONS

Simpson et al.; U.S. Appl. No. 14/899,893 entitled "Identification of elastic lamina to guide interventional therapy," filed Dec. 18, 2015.

Gupta et al.; U.S. Appl. No. 14/776,749 entitled "Tissue collection device for catheter," filed Sep. 15, 2015.

Smith et al.; U.S. Appl. No. 14/776,748 entitled "Optical pressure sensor assembly," filed Sep. 15, 2015.

Aziz et al.; Chronic total occlusions—a stiff challenge requiring a major breakthrough: is there light at the end of the tunnel?; Heart; vol. 91; suppl. III; pp. 42-48; Jun. 2005.

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Linares et al.; Arbitrary single-mode coupling by tapered and nontapered grin fiber lenses; Applied Optics; vol. 29; No. 28; pp. 4003-4007; Oct. 1, 1990.

Sharma et al.; Optical coherence tomography based on an all-fiber autocorrelator using probe-end reflection as reference; CWJ13; San Francisco, California; CLEO May 16, 2004; 4 pages.

Suparno et al.; Light scattering with single-mode fiber collimators; Applied Optics; vol. 33; No. 30; pp. 7200-7205; Oct. 20, 1994.

Han et al.; In situ Frog Retina Imaging Using Common-Path OCT with a Gold-Coated Bare Fiber Probe; CFM6; San Jose, California; CLEO, May 4, 2008; 2 pages.

Muller et al.; Time-gated infrared fourier-domain optical coherence tomography; CFM5; San Jose, California; CLEO May 4, 2008; 2 pages.

Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Rosenthal et al.; U.S. Appl. No. 15/354,898 entitled "Atherectomy catheter with laterally-displaceable tip," filed Nov. 17, 2017.

Patel et al.; U.S. Appl. No. 15/354,842 entitled "Atherectomy catheters and occlusion crossing devices," filed Nov. 17, 2016.

Patel et al.; U.S. Appl. No. 15/162,330 entitled "Atherectomy catheters with longitudinally displaceable drive shafts," filed May 23, 2016.

Spencer et al.; U.S. Appl. No. 15/162,353 entitled "Occlusion-crossing devices, atherectomy devices, and imaging," filed May 23, 2016.

Tachibana et al.; U.S. Appl. No. 15/162,391 entitled "Atherectomy catheter drive assemblies," filed May 23, 2016.

Shinkle et al.; Evaluation of stent placement and outcomes with optical coherence tomography; Interv. Cardiol.; 2(4); pp. 535-543; (manuscript version, 12 pages); Aug. 2010.

Patel et al.; U.S. Appl. No. 15/324,325 entitled "High speed chronic total occulusion crossing devices," filed Jan. 6, 2017.

Kankaria; U.S. Appl. No. 15/419,815 entitled "Optical coherence tomography with graded index fiber for biological imaging," filed Jan. 30, 2017.

Simpson et al.; U.S. Appl. No. 15/434,758 entitled "Occlusion-crossing devices, imaging, and atherectomy devices," filed Feb. 16, 2017.

Simpson et al.; U.S. Appl. No. 15/457,960 entitled "Atherectomy catheters devices having multi-channel bushings," filed Mar. 13, 2017.

Patel et al.; U.S. Appl. No. 15/480,238 entitled "Guidewire positioning catheter," filed Apr. 5, 2017.

* cited by examiner

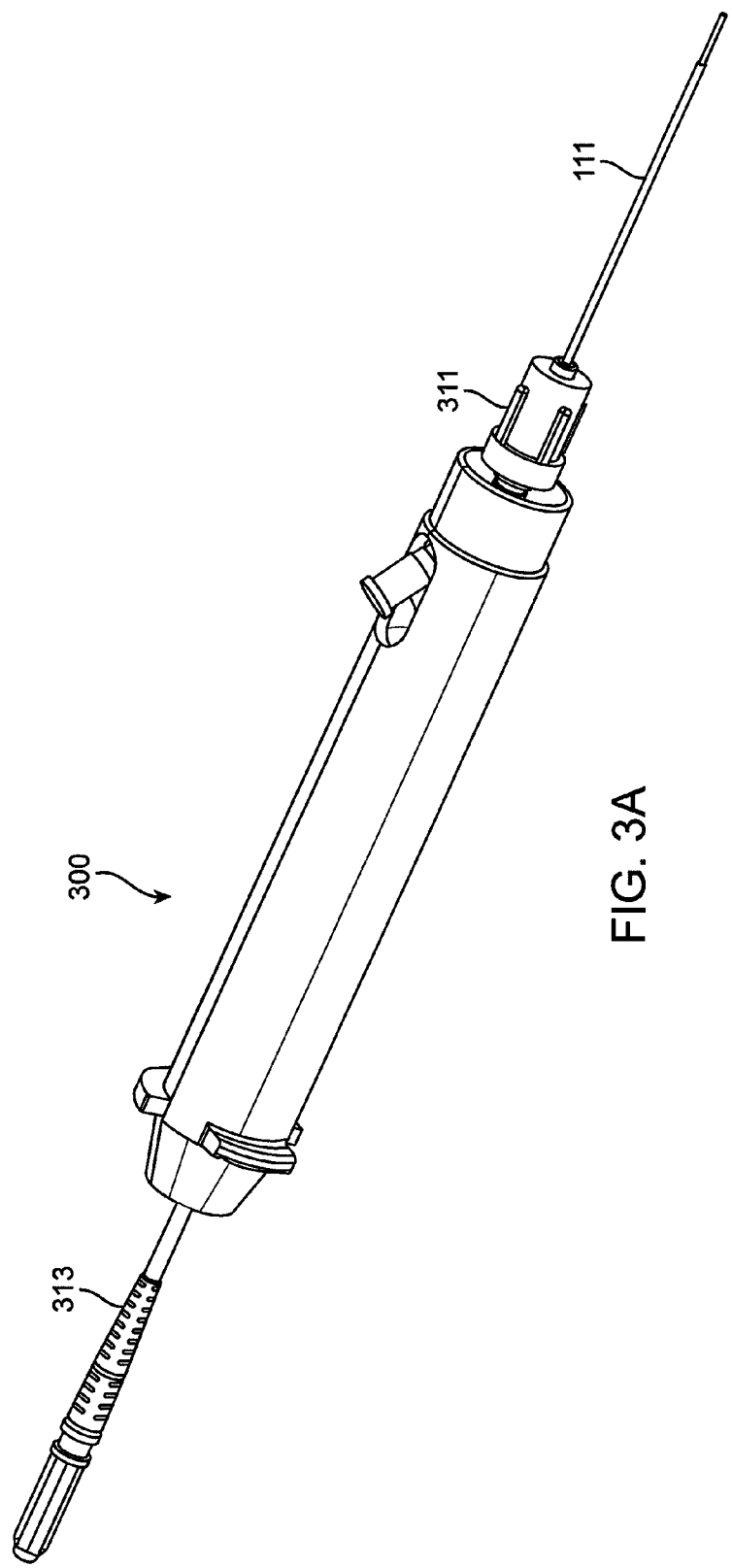

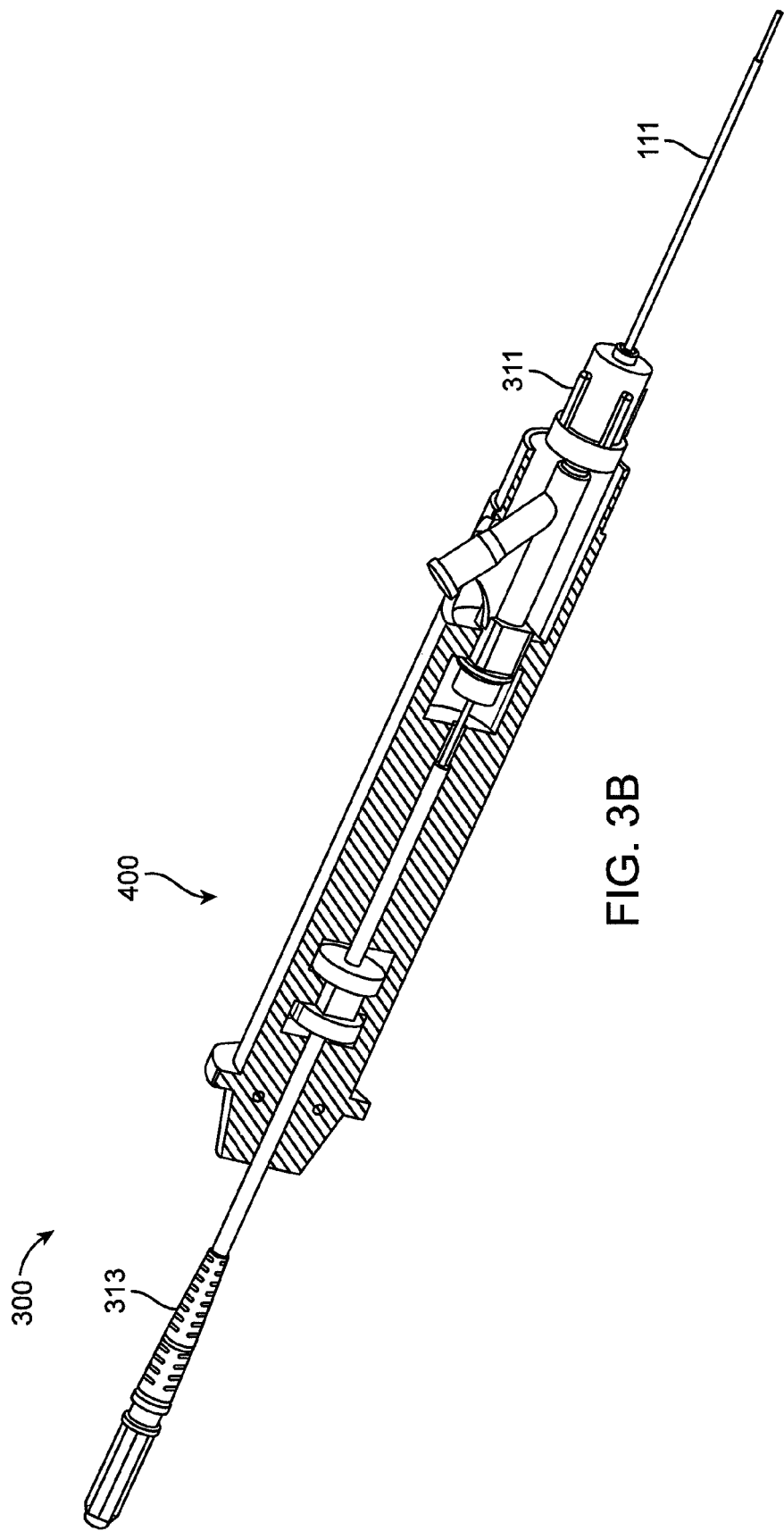

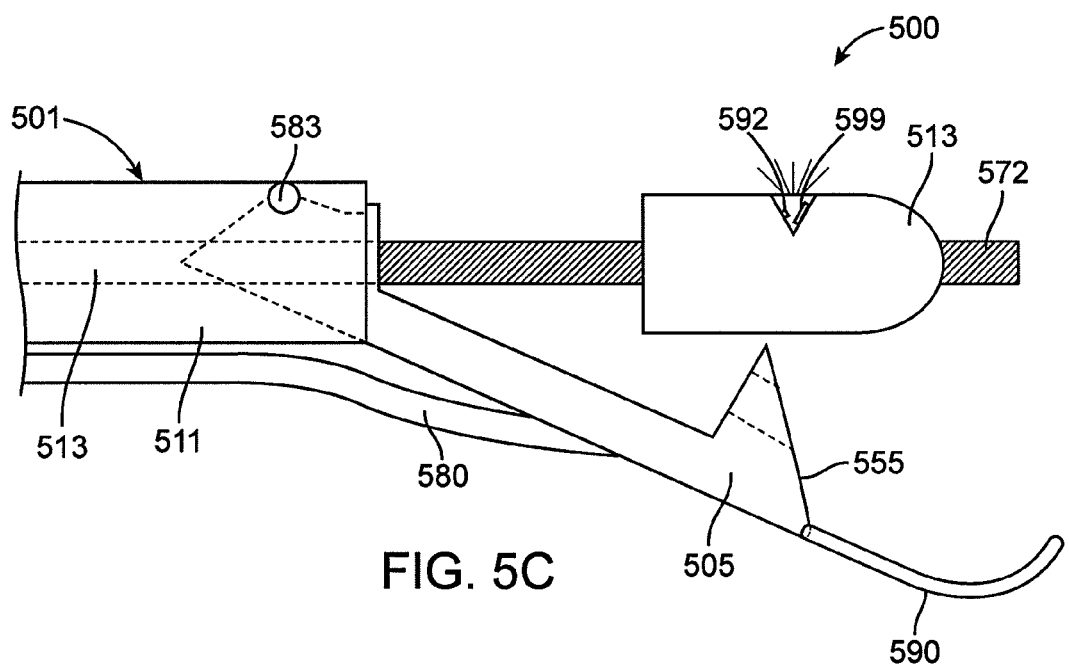
FIG. 5C
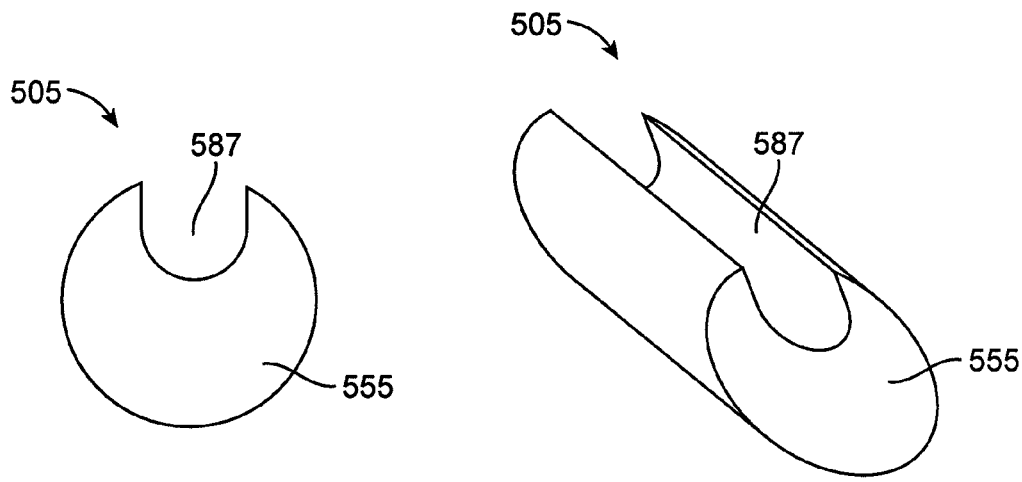
FIG. 5D
FIG. 5E

CHRONIC TOTAL OCCLUSION CROSSING DEVICES WITH IMAGING

INCORPORATION BY REFERENCE

All publications and patent applications mentioned in this specification are herein incorporated by reference to the same extent as if each individual publication or patent application was specifically and individually indicated to be incorporated by reference.

BACKGROUND

Peripheral artery disease (PAD) and coronary artery disease (CAD) affect millions of people in the United States alone. PAD and CAD are silent, dangerous diseases that can have catastrophic consequences when left untreated. CAD is the leading cause of death for in the United States while PAD is the leading cause of amputation in patients over 50 and is responsible for approximately 160,000 amputations in the United States each year.

Coronary artery disease (CAD) and Peripheral artery disease (PAD) are both caused by the progressive narrowing of the blood vessels most often caused by atherosclerosis, the collection of plaque or a fatty substance along the inner lining of the artery wall. Over time, this substance hardens and thickens, which may interfere with blood circulation to the arms, legs, stomach and kidneys. This narrowing forms an occlusion, completely or partially restricting flow through the artery. Blood circulation to the brain and heart may be reduced, increasing the risk for stroke and heart disease.

Interventional treatments for CAD and PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked. Other treatments may include angioplasty to open the artery. For example, a balloon angioplasty typically involves insertion of a catheter into a leg or arm artery and positioning the catheter such that the balloon resides within the blockage. The balloon, connected to the catheter, is expanded to open the artery. Surgeons may then place a wire mesh tube, called a stent, at the area of blockage to keep the artery open.

Such minimally invasive techniques (e.g., atherectomy, angioplasty, etc.) typically involve the placement of a guidewire through the occlusion. Using the guidewire, one or more interventional devices may be positioned to remove or displace the occlusion. Unfortunately, placement of the guidewire, while critical for effective treatment, may be difficult. In particular, when placing a guidewire across an occlusion, it may be difficult to pass the guidewire through the occlusion while avoiding damage to the artery. For example, it is often difficult to prevent the guidewire from directing out of the lumen into the adventitia and surrounding tissues, potentially damaging the vessel and preventing effective treatment of the occlusion.

As a result, occlusion-crossing devices, intended to assist in the passing of the guidewire through the occlusion, have been developed. Many of the devices, however, are ill equipped to be used with imaging, thereby making placement of the guidewire cumbersome and difficult. Moreover, many of the occlusion-crossing devices are too large to be used in small-diameter peripheral arteries or in coronary arteries.

Accordingly, occlusion crossing catheter devices designed to address some of these concerns are described herein.

SUMMARY OF THE DISCLOSURE

Described herein are occlusion-crossing devices having a low profile so as to be usable in small vessels, such as coronary arteries.

In general, in one embodiment, an imaging device includes a hollow flexible shaft having a central longitudinal axis and an imaging window therein. An optical fiber extends within the hollow flexible shaft substantially along the central axis. A distal tip of the optical fiber is attached to the hollow flexible shaft and aligned with the imaging window so as to transfer an optical coherence tomography signal through the imaging window. A handle is attached to the hollow flexible shaft configured rotate the hollow flexible shaft at speeds of greater than 1,000 rpm.

This and other embodiments may include one or more of the following features. The optical fiber can extend substantially along the central axis for the entire length of the fiber. The device can be less than 0.1 inches, 0.08 inches, or 0.05 inches in diameter. The hollow flexible shaft can be made of tungsten. The hollow flexible shaft can be made of multiple layers of wound filars. The filars can be counterwound. The hollow flexible shaft can further include a mirror therein configured to reflect light from the optical fiber into adjacent tissue. The device can include an outer sheath extending around the hollow flexible shaft. The outer sheath can include an optically clear annular section at the distal end thereof.

In general, in one embodiment, an imaging assembly includes a catheter having a cutter and a lumen extending the length of the catheter. A hollow flexible shaft is configured to be inserted within the lumen of the catheter. The hollow flexible shaft includes a central longitudinal axis and an imaging window therein. An optical fiber extends within the hollow flexible shaft substantially along the central axis. A distal tip of the optical fiber is attached to the hollow flexible shaft and aligned with the imaging window so as to transfer an optical coherence tomography signal through the imaging window.

This and other embodiments can include one or more of the following features. The catheter can include a cutter at a distal end. The hollow flexible shaft can further include a handle attached thereto configured rotate the hollow flexible shaft at speeds of greater than 1,000 rpm. The optical fiber can extend substantially along the central axis for the entire length of the fiber. The imaging assembly can further include an outer sheath extending around the hollow flexible shaft. The outer sheath can include an optically clear annular section at the distal end thereof. The hollow flexible shaft can be made of tungsten. The hollow flexible shaft can be made of multiple layers of wound filars. The filars can be counterwound. The hollow flexible shaft can further include a mirror attached to the distal end configured to reflect light from the optical fiber into adjacent tissue.

In general, in one embodiment, a method of imaging a body lumen includes: inserting a catheter into the body lumen; inserting an imaging device into a lumen of the catheter, the imaging device including a hollow flexible shaft having a central longitudinal axis with an imaging window therein and an optical fiber extending within the hollow flexible shaft and attached to the hollow flexible shaft, the optical fiber extending substantially along the central longitudinal axis; rotating the hollow flexible shaft within the lumen of the catheter; and collecting images of the body lumen through the imaging window with the optical fiber.

This and other embodiments can include one or more of the following features. Rotating the hollow flexible shaft within the lumen can include rotating the hollow flexible shaft at speeds of greater than 1,000 rpm. Collecting images of the body lumen can include collecting images of the body lumen at rates of greater than 10 frames per minute. The body lumen can be a coronary artery or a peripheral artery. The catheter can include a cutter thereon, and the method can further include cutting tissue of the body lumen with the catheter to pass through an occlusion in the body lumen. The method can further include removing the imaging device from the lumen of the catheter and advancing a guidewire through the lumen of the catheter after passing the cutter through the occlusion.

In general, in one embodiment, an occlusion crossing device includes a rotatable hollow flexible shaft having a central longitudinal axis and an imaging window therein. The occlusion crossing device further includes an optical fiber extending within the hollow flexible shaft substantially along the central axis. A distal tip of the optical fiber is aligned with the imaging window so as to transfer an optical coherence tomography signal through the imaging window. A cutter is attached to a distal end of the hollow flexible shaft.

This and other embodiments can include one or more of the following features. The optical fiber can extend substantially along the central axis for the entire length of the fiber. The occlusion crossing device can further include an outer sheath extending around the hollow flexible shaft. A monorail guidewire can be attached to the outer sheath. The outer sheath can include an optically clear annular section at the distal end thereof. The hollow flexible shaft can be made of tungsten. The hollow flexible shaft can be made of multiple layers of wound filars. The filars can be counterwound. The device can be less than 0.1, less than 0.08, or less than 0.05 inches in diameter. The cutter can include a fluted distal end. The cutter can further include a slanted proximal end and a mirror attached to the proximal end configured to reflect light from the optical fiber into adjacent tissue. The optical fiber can be configured to remain stationary relative to the hollow flexible shaft. The optical fiber can be attached to the hollow flexible shaft and configured to rotate therewith. The occlusion crossing device can further include a handle attached to the flexible shaft configured to rotate the hollow flexible shaft at speeds of greater than 1,000 rpm.

In general, in one embodiment, a method of crossing an occlusion in a blood vessel includes: inserting an occlusion crossing device into the vessel, the occlusion crossing device including a hollow flexible shaft having a central longitudinal axis and an imaging window therein, an optical fiber extending within the hollow flexible shaft substantially along the central axis to transfer an optical coherence tomography signal, and a cutter attached to a distal end of the hollow flexible shaft; rotating the hollow flexible shaft and cutter so as to separate tissue of the occlusion; collecting images of the vessel through the imaging window with the optical fiber; and passing the cutter through the occlusion.

This and other embodiments can include one or more of the following features. Rotating the flexible shaft and cutter can include rotating at speeds of greater than 1,000 rpm. Collecting images of the vessel can include collecting images at rates of greater than 10 frames per minute. The method can further include rotating the optical fiber with the hollow flexible shaft. Rotating the hollow flexible shaft can include rotating the imaging shaft while keeping the fiber rotationally fixed. The vessel can be a coronary artery or a peripheral artery.

In general, in one embodiment, an occlusion crossing device includes an elongate body and a drive shaft extending through the elongate body having a perforating tip attached thereto. The occlusion crossing device further includes a deflectable tip having a wedged distal end attached to the elongate body and a guidewire lumen extending through the deflectable tip.

This and other embodiments can include one or more of the following features. The occlusion crossing device can further include an imaging element attached to the drive shaft. The imaging element can be an optical coherence tomography imaging element. The deflectable tip can be configured to be deflected by axial movement of the drive shaft. The device can be less than 0.1 inches, less than 0.08 inches, or less than 0.05 inches in diameter.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A shows an outer view of the device. FIG. 1B shows a close-up of the imaging and cutting portion of the device of FIG. 1A. FIG. 1C is a cross-section of the device of FIG. 1A.

FIGS. 3A-3B show a handle for use with the device of FIGS. 1A-1C. FIG. 3A is an outer view of the handle. FIG. 3B is a cross-section of the handle.

FIGS. 5A-5E show an exemplary occlusion crossing device with a deflectable wedged distal tip. FIG. 5A shows a cross-section of the device with the deflectable tip in a closed configuration. FIG. 5B shows a cross-section of the device with the deflectable tip in an open configuration. FIG. 5C shows a cross-section of the device with the deflectable tip in an open configuration and the cutting edge extended distally. FIG. 5D is an end-view of the deflectable tip. FIG. 5E is an isometric view of the deflectable tip.

DETAILED DESCRIPTION

Described herein are occlusion-crossing devices having a low profile so as to be usable in small-diameter arteries and coronary arteries. In general, the devices described herein can have on-board imaging, such as optical coherence tomography (OCT) imaging. The optical fiber for the OCT imaging can substantially along the central of the device, thereby decreasing the profile of the device and allowing for single direction rotation at high speeds. A monorail guidewire lumen can be attached to the devices described herein.

In some embodiments, a catheter device, such as an occlusion-crossing device, can include an imaging shaft with a fiber running down the center of the catheter. The fiber can be rotated with a fiber optic junction so as to rotatable at high speeds in a single direction. A monorail guidewire lumen can extend along the outside of the device parallel to the central axis of the catheter.

Figure 1A:
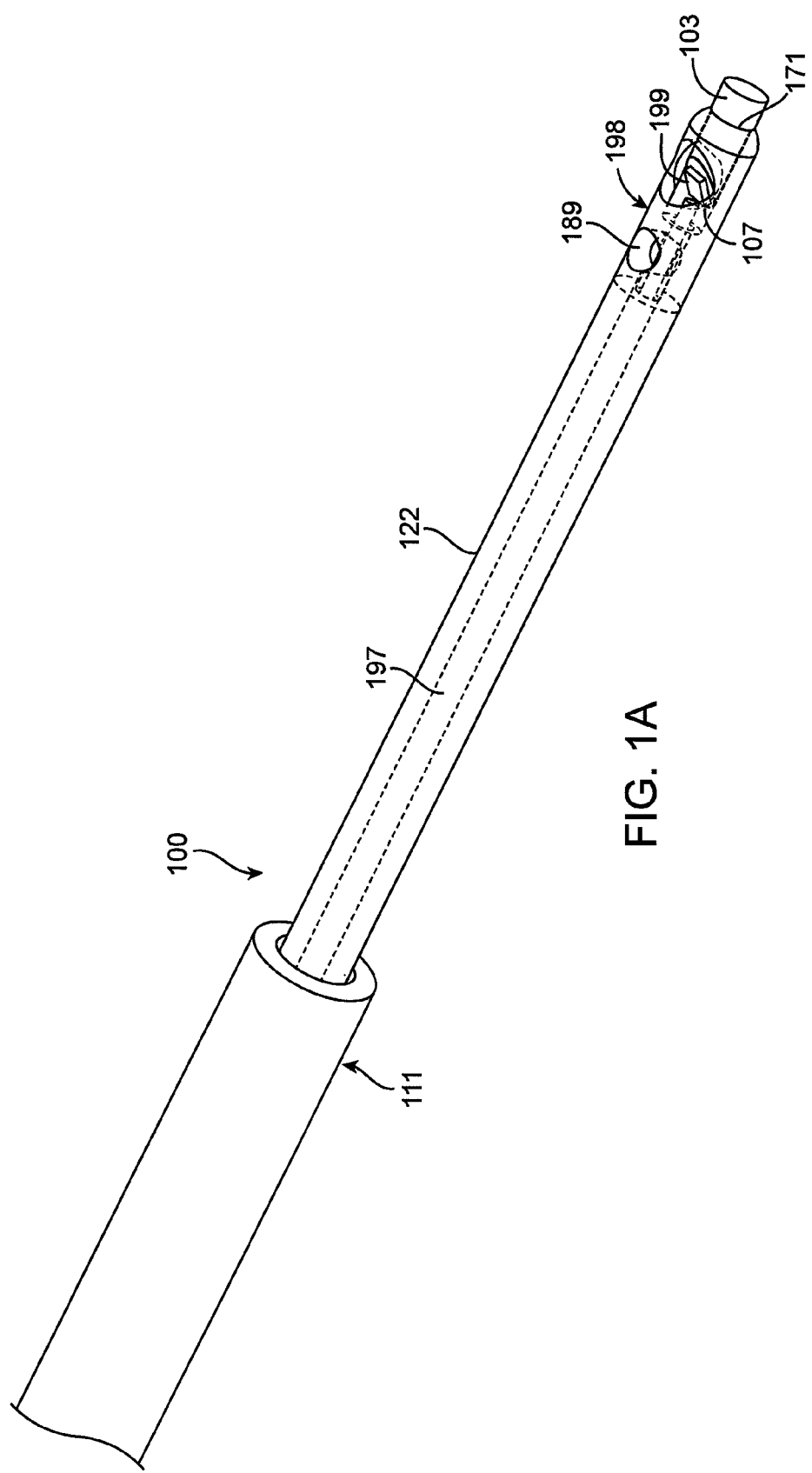
FIGS. 1A-1C show an occlusion crossing device having an optical fiber for imaging running down the center of the device.
Figure 1B:
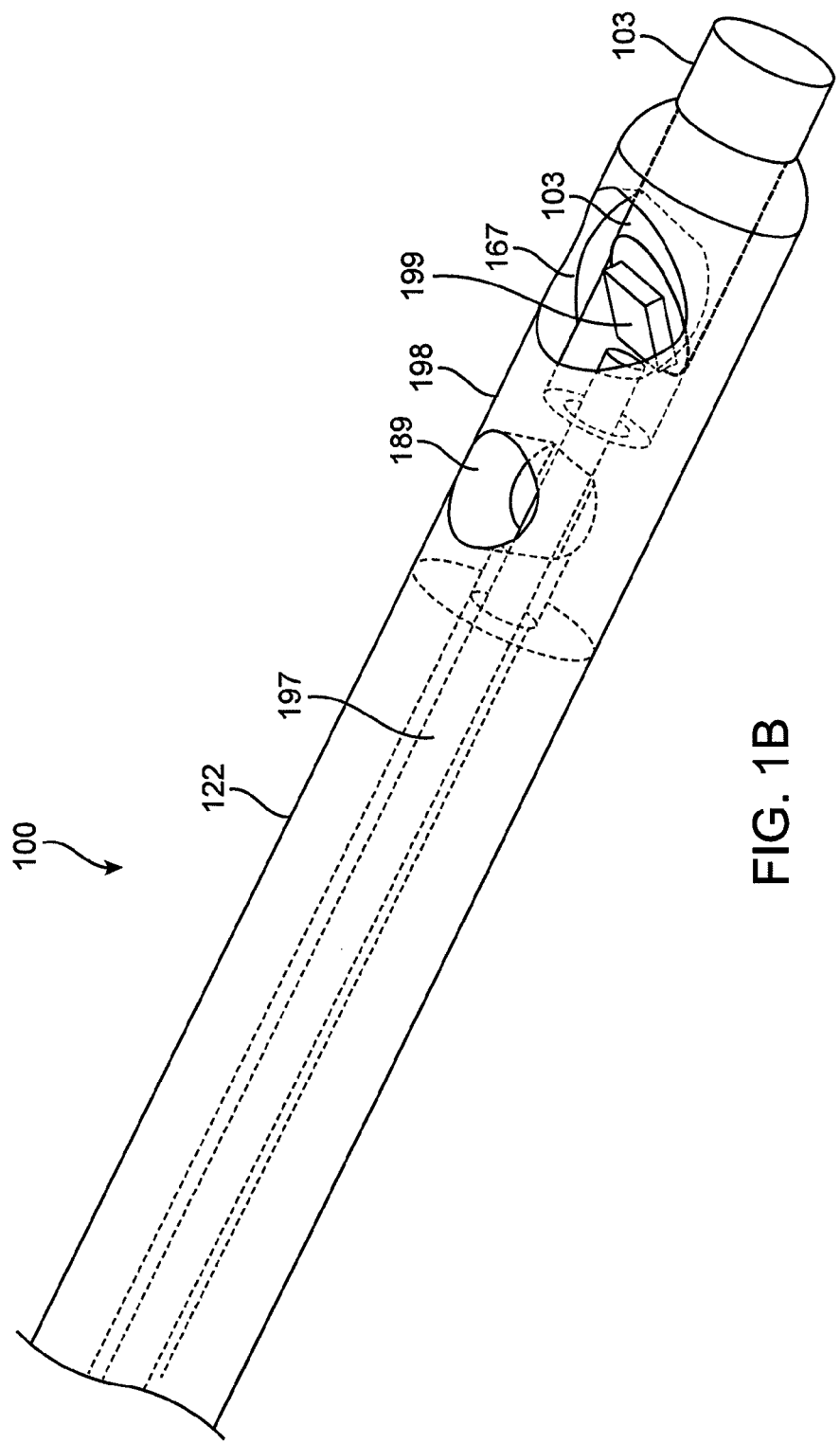
Figure 1C:
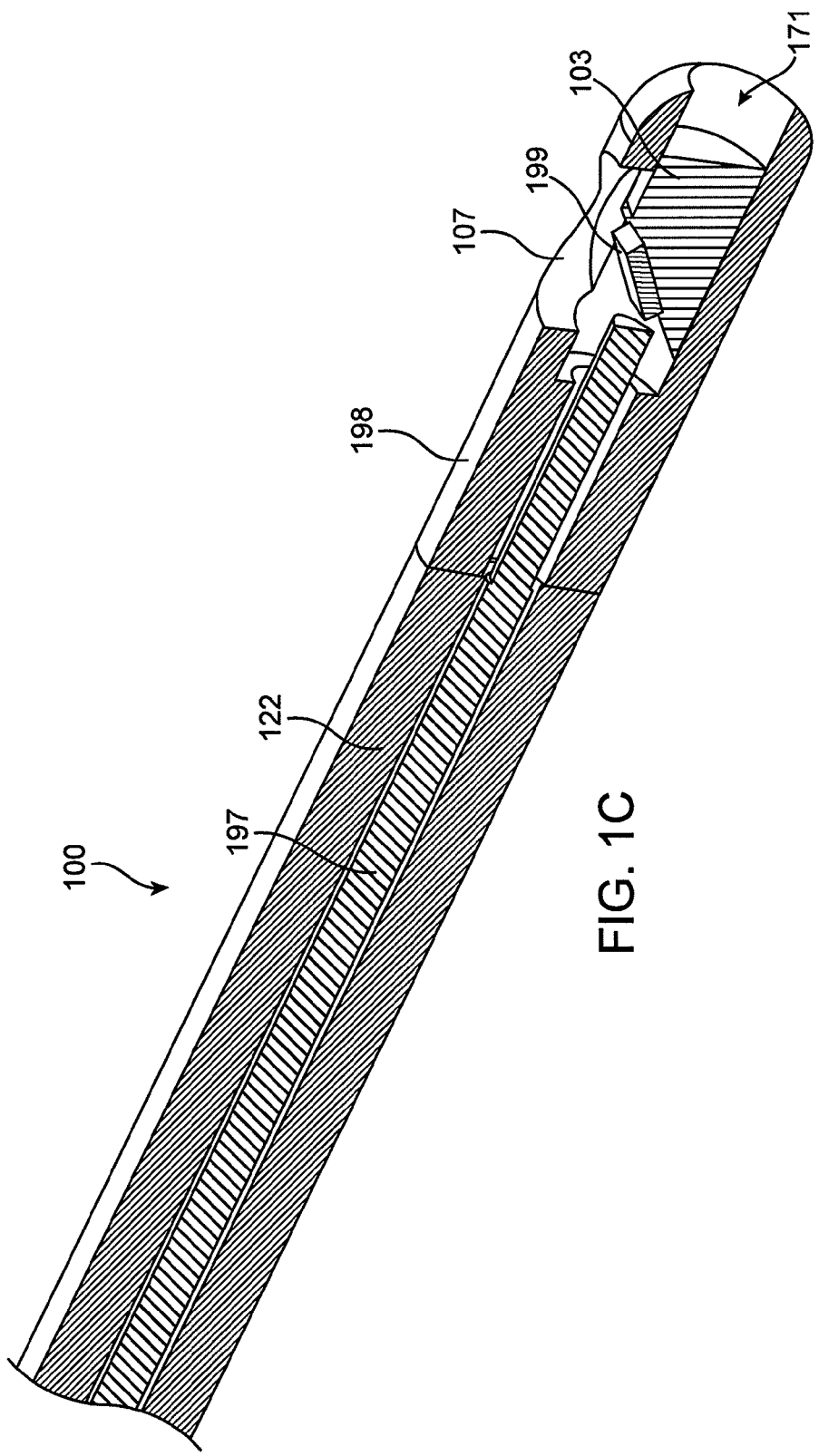

Referring to FIGS. 1A-1C, an exemplary catheter device 100 is shown. The catheter device 100 can include an imaging shaft 122. The imaging shaft 122 can be hollow and can have an inner diameter of approximately 0.005" to 0.010", e.g., 0.009" or 0.008". The imaging shaft 122 could have an outer diameter of approximately 0.01-0.038". Further, the imaging shaft 122 can be sized to work inside the lumen of another catheter, e.g., a catheter having a lumen diameter of 0.014", 0.018", or 0.035". In some embodiments, the imaging shaft 122 can be made of a wire material, such as stainless steel or tungsten, or, alternatively can be made from a flexible tube such as a plastic or laser cut tube. Further, in some embodiments, the imaging shaft 122 can include multiple filar layers. For example, the imaging shaft 122 can include two layers of 8 counterwound filars per layer or three layers of 12 counterwound filars per layer or the number of filars could vary by layer (e.g., 12 filars over 8 filars). Advantageously, by using multiple layers of filars, the imaging shaft 122 can be configured to rotate at speeds of over 1,000 rpm.

The catheter 100 can further include an imaging element. Thus, an optical fiber 197 can extend through the hollow imaging shaft 122 such that the optical fiber 197 runs substantially along the central axis of the catheter for the entire length of the fiber 197. The fiber 197 can be attached at the distal end of the imaging shaft 122 (such as in the bulb 198 described below), but can be otherwise free to float within the imaging shaft 122. The imaging fiber 197 can transfer an optical coherence tomography (OCT) signal for imaging of the vessel in which the device 100 is placed. In some embodiments, the imaging fiber 197 can have a polyimide coating therearound within the length of the shaft 122 to support and protect the fiber 197 as it spins within the shaft 122.

The optical fiber 197 can end in a hollow bulb 198 at the end of the imaging shaft 122. The bulb 198 can be made of the same material as the imaging shaft 122, such as stainless steel. The bulb 198 can include a mirror 199 oriented at an angle (such as a 30-60 degree angle, e.g., 45 degrees) with respect to the central axis of the fiber 197 such that light coming out of the fiber 197 will bounce off the mirror 197 and into the adjacent tissue. The bulb 198 can include glue therein to hold the distal end of the optical fiber 197 in place. The glue can have a refractive index configured to be appropriately mismatched with the refractive index of the fiber, as described in U.S. patent application Ser. No. 12/790,703, titled "OPTICAL COHERENCE TOMOGRAPHY FOR BIOLOGICAL IMAGING," filed May 28, 2010, Publication No. US-2010-0305452-A1; and International Patent Application titled "OPTICAL COHERENCE TOMOGRAPHY WITH GRADED INDEX FIBER FOR BIOLOGICAL IMAGING," filed herewith, both of which are incorporated by reference in their entireties. Further, the glue can have a meniscus shape along its outer edge, as described in International Patent Application titled "OPTICAL COHERENCE TOMOGRAPHY WITH GRADED INDEX FIBER FOR BIOLOGICAL IMAGING," filed herewith, already incorporated by reference herein. The meniscus shape can advantageously ensure that the light reflected back from the surface of the glue and back into the fiber 197 is significantly less than the light referenced.

The bulb 198 can further include an imaging window 107 therein aligned with the mirror 199 such that the light bouncing off the mirror can travel therethrough into the tissue. In some embodiments, the bulb 198 can include a second hole 189 therein that is proximal to the window 107. The second hole 189 can be configured to allow for the placement of additional glue to hold the fiber 197 in place.

Figure 1D:
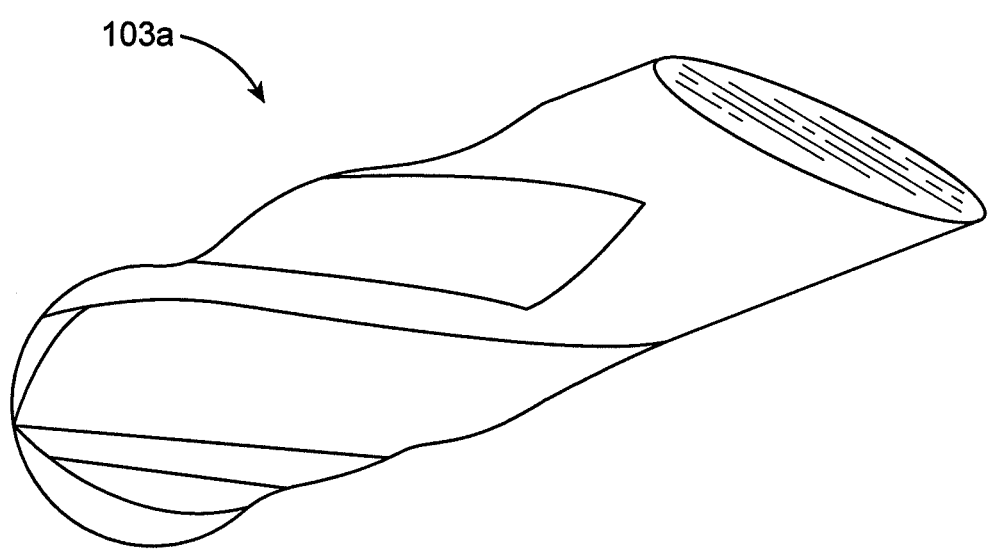
FIGS. 1D-1E show exemplary cutting tips for use with the device of FIG. 1A.
Figure 1E:
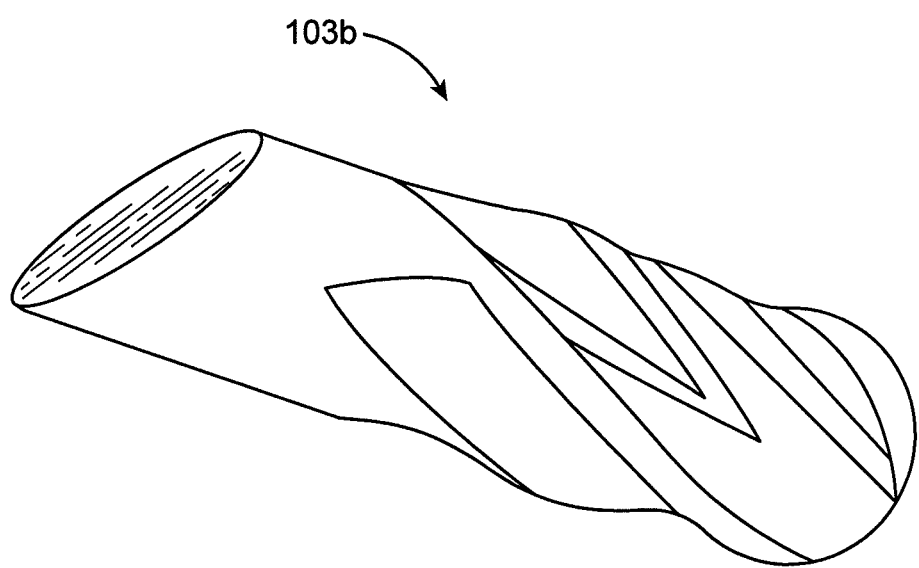

Referring to FIGS. 1B and 1D-E, in some embodiments, the bulb 198 can include a cutter 103 connected to the distal end thereof. The cutter can be configured, for example, to separate, dissect, or shred tissue. As shown in FIG. 1B, the cutter 103 can have proximal end oriented an angle so as to support the angled mirror 199. Further, the cutter 103 can have a distal sharp cutting edge that extends out of a distal hole 171 in the bulb 198. In some embodiments, the cutter 103 can include multiple sharp flutes that come to a point in the center of the device. Two exemplary cutters 103a, 103b are shown in FIGS. 1D and 1E. The cutter 103a of FIG. 1D includes two spiral flutes while the cutter 103b of FIG. 1D includes four spiral flutes.

The imaging shaft 122, and thus the optical fiber 197, can be configured to rotate at high speeds, such as greater than 1,000 rpm, in a single direction to provide OCT imaging around the inner circumference of the vessel. Such high speed rotation in a single direction (as opposed to requiring rotation alternately in both directions to manage the optical fiber) allows for the gathering of image data more quickly, thereby providing more accurate and up-to-date images during use of the device 100. For example, images can be generated at a rate of greater than 10 frames per section (fps), such as greater than 10 fps, such as approximately 16.67 fps. In an exemplary embodiment, the rate of Laser sweep, such as approximately 20 KHz, can be configured to keep up with at 16.67 frames per second with about 1200 lines per frame.

Figure 2A:
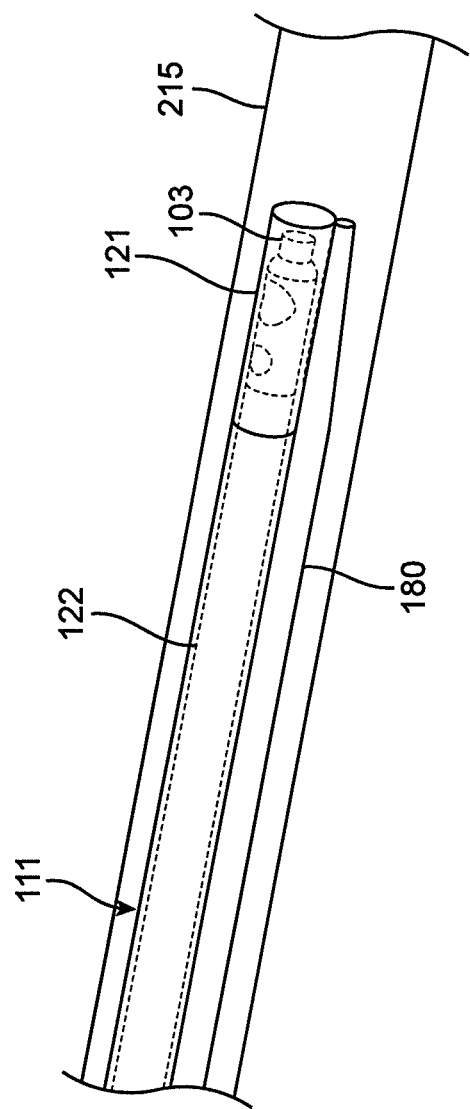
FIG. 2A shows placement of the device of FIGS. 1A-1C in a passive configuration in a vessel.
Figure 2B:
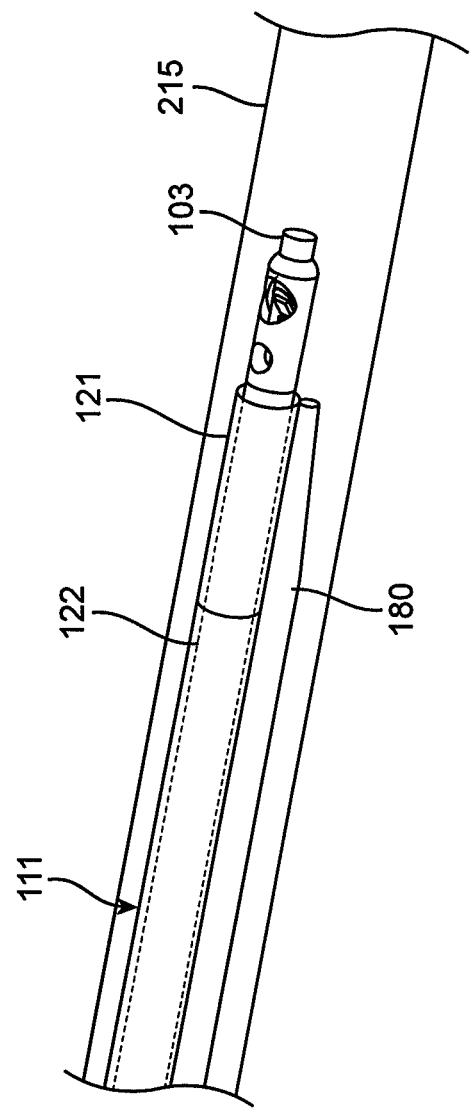
FIG. 2B shows placement of the device of FIGS. 1A-1C in an active configuration in a vessel.

The catheter 100 can further include a sheath 111, such as a sheath that is less than 0.060" in diameter, such as less than 0.050" in diameter. The sheath 111 can extend annularly around the imaging shaft 197. The sheath 111 can include an optically clear annular section 121 (e.g., optically transparent at a wavelength of 1300 nm) at the distal end thereof, as shown in FIGS. 2A-2B. The optically clear annular section 121 can be made, for example, of tecothane or fluorinated ethylene propylene (FEP). In some embodiments, the optically clear annular section 121 can have a refractive index of between 1.35 and 1.45 that is close to the refractive index of saline, thereby reducing the back-reflection caused when saline is flushed through the sheath 111. The optically clear annular section 121 can advantageously allow for imaging with the OCT fiber 197 without extending the imaging shaft 122 out of the sheath 111, thereby allowing for imaging without cutting. Thus, the imaging shaft 197 can rotate within the sheath 111 and move axially (proximally and distally) within the sheath 111. Allowing the imaging shaft 122 to rotate and translate within the sheath 111 advantageously allows such actions to occur without changing the position of the sheath 111 when in use within a vessel.

Referring to FIGS. 2A-2B, the catheter 100 can further include a guidewire lumen 180, which can be a monorail extending along the distal end of the sheath 111. The guidewire lumen 180 can have an inner diameter, for example, of 0.010" to 0.020", such as approximately 0.016" in diameter, such as to hold, for example, a 0.014" guidewire. The guidewire lumen 180 can be made, for example, of polyimide. In other embodiments, the catheter 100 can be fabricated or used without a guidewire lumen. For example, the catheter 100 (including the sheath 111) can be inserted into the vessel, tunneled through an occlusion through the use of the cutter 103, and then the imaging shaft 122 can be removed, leaving the sheath in place. A guidewire could then be inserted through the sheath 111 to get the guidewire across the occlusion.

Advantageously, because the optical fiber 197 runs through the center of the device 100, the device 100 can be small in diameter. For example, the outer diameter of the device 100 (including the sheath and monorail) can be less than 0.10", such as less than 0.08", such as less than 0.07", less than 0.06", or less than 0.05". Accordingly, the device 100 can advantageously be used in small-diameter peripheral arteries and coronary arteries.

Referring to FIGS. 2A-2B, in use, the device 100 can be inserted into a vessel 215 in a passive configuration where the imaging shaft 122 and cutter 103 are entirely within the sheath 111 (as shown in FIG. 2A). To do so, the device 100 can be extended over a guidewire that has been placed within the vessel (i.e., the guidewire lumen 180 can extend over the guidewire). The imaging shaft 122 can be rotated, thereby obtaining an image with the fiber 197 through the clear annular section 121 of the sheath 111.

In some embodiments, the resulting image will have a wire artifact caused by the guidewire obstructing the OCT beam as the imaging shaft 122 is rotated. The wire artifact in the image can be used to determine the direction to point or orient the catheter. That is, in some embodiments, the wire artifact can be used to align the device 100 with a fluoroscopic image and/or to orient a fixed jog or deflection point in the catheter that has a set orientation relative to the guidewire lumen. Alignment of markers with fluoroscope images and orientation of jogged portions of a catheter using markers is described further in U.S. patent application Ser. No. 13/433,049, titled "OCCLUSION-CROSSING DEVICES, IMAGING, AND ATHERECTOMY DEVICES," filed Mar. 28, 2012, Publication No. US-2012-0253186-A1, the entirety of which is incorporated herein by reference.

The guidewire can then be retracted until the wire artifact in the image is gone, thereby fully removing the guidewire from potential entanglement with the rotating cutter 103.

The imaging shaft 122 can then be extended distally, thereby extending the cutter 103 distally until the cutter 103 is past the distal end of the sheath 111 such that the device 100 takes an active configuration (as shown in FIG. 2B). The imaging shaft 122 can then be rotated, thereby both imaging the vessel and cutting through plaque or tissue in the vessel. The imaging shaft 122 can then be retracted into the sheath 111. The guidewire can then be advanced, and the process repeated until the device 100 has crossed the occlusion.

The rotation or translation of the imaging shaft 122 can be controlled through a handle attached the device 100. An exemplary handle 300 is shown in FIGS. 3A-3B. The handle 300 can include a rotational torque knob 311 attachable to the sheath 111 and configured to provide torque to the sheath 111. In some embodiments, the handle 300 can include a flush port, such as an RHV style flush port. The handle 300 can further include a mechanism, such as a fiber optic rotary junction, therein configured to allow for rotation of the shaft 122 and optical fiber 197 without rotating the fiber from the light source. Further, the handle 300 (or the catheter 100) can be configured to be attached to a drive system, such as through an optical connector 313. The drive system can include a rotary optical junction configured to rotate the fiber. Exemplary drive systems that could be used in conjunction with the devices herein are described in U.S. patent application Ser. No. 13/654,357, titled "ATHERECTOMY CATHETERS AND NON-CONTACT ACTUATION MECHANISM FOR CATHETERS," filed Oct. 17, 2012 and International Patent Application titled "ATHERECTOMY CATHETER DRIVE ASSEMBLIES," filed herewith, each incorporated herein by reference in its entirety.

In some embodiments, the device 100 can be fabricated without the cutter 103, and the device 100 can instead be used as an imaging guidewire, imaging wire, or imaging component that can be placed within another device, such as an occlusion crossing device, atherectomy device, guide catheter, guiding sheath, over-the-wire balloon catheter, or support catheter, to provide imaging during procedures. In such instances, the device 100 could be used with the sheath 111 or without (and the device in which device 100 is inserted could act as a sheath). Further, in such instances, the catheter within which the device 100 is placed can include a cutter. Exemplary devices with which the device 100 could be used as an imaging guidewire or imaging component are described in: U.S. patent application Ser. No. 12/689,748, titled "GUIDEWIRE POSITIONING CATHETER," filed Jan. 19, 2010, Publication No. US-2010-0274270-A1; U.S. patent application Ser. No. 12/108,433, titled "CATHETER SYSTEM AND METHOD FOR BORING THROUGH BLOCKED VASCULAR PASSAGES," filed Apr. 23, 2008, now U.S. Pat. No. 8,062,316; U.S. patent application Ser. No. 12/829,267, titled "CATHETER-BASED OFF-AXIS OPTICAL COHERENCE TOMOGRAPHY IMAGING SYSTEM," filed Jul. 1, 2010, Publication No. US-2010-0021926-A1; U.S. patent application Ser. No. 13/433,049, titled "OCCLUSION-CROSSING DEVICES, IMAGING, AND ATHERECTOMY DEVICES," filed Mar. 28, 2012, Publication No. US-2012-0253186-A1; International Patent Application titled "OCCLUSION-CROSSING DEVICES," filed herewith; U.S. patent application Ser. No. 12/829,277, titled "ATHERECTOMY CATHETER WITH LATERALLY-DISPLACEABLE TIP," filed Jul. 1, 2010, Publication No. US-2011-0004107-A1; U.S. patent application Ser. No. 13/175,232, titled "ATHERECTOMY CATHETERS WITH LONGITUDINALLY DISPLACEABLE DRIVE SHAFTS," filed Jul. 1, 2011, Publication No. US-2012-0046679-A1; U.S. patent application Ser. No. 13/654,357, titled "ATHERECTOMY CATHETERS AND NON-CONTACT ACTUATION MECHANISM FOR CATHETERS," filed Oct. 17, 2012; U.S. patent application Ser. No. 13/675,867, titled "OCCLUSION-CROSSING DEVICES, ATHERECTOMY DEVICES, AND IMAGING," filed Nov. 13, 2012; International Patent Application titled "ATHERECTOMY CATHETERS WITH IMAGING," filed herewith; International Patent Application titled "BALLOON ATHERECTOMY CATHETERS WITH IMAGING," filed herewith, the entireties of which are incorporated herein by reference.

In some embodiments, an occlusion crossing device can include a stationary optical fiber for optical coherence tomography imaging.

Figure 4A:
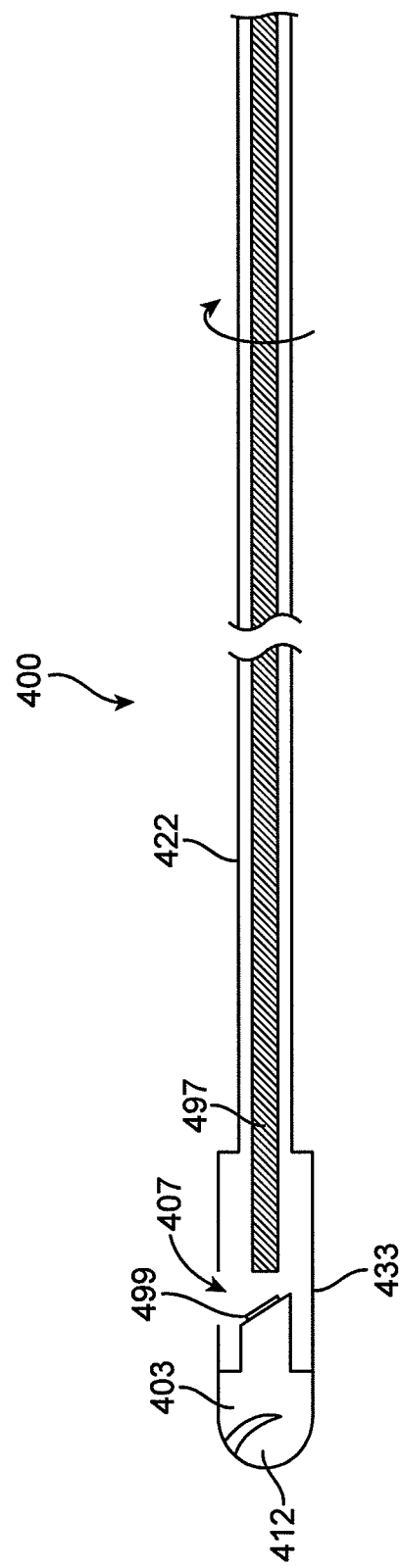
FIG. 4A shows a cross-section of an exemplary occlusion crossing device having a stationary optical fiber and rotating outer sheath.
Figure 4B:
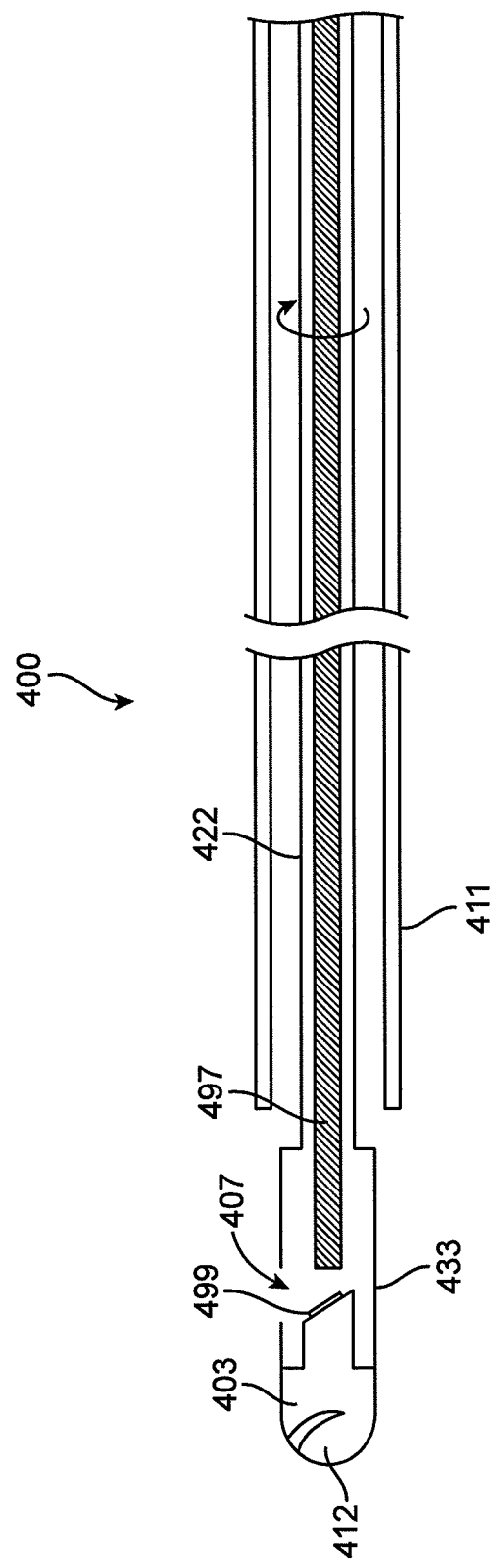
FIG. 4B shows the device of FIG. 4A with an outer sheath therearound.

For example, referring to FIG. 4A, an occlusion crossing device 400 can include a hollow rotatable imaging shaft 422. The rotatable imaging shaft 422 can be made of a coiled structure that can be optimized (such as the number of filars or the filar size) to provide the desired stiffness.

The occlusion crossing device 400 can further include an imaging element. Thus, an optical fiber 497 can extend through the hollow rotatable imaging shaft 422 so as to extend substantially along the central axis of the device 400.

The optical fiber 497 can be configured to as to stay stationary during rotation of the imaging shaft 422. For example, the optical fiber 492 can be attached to a bearing at the distal end of the imaging shaft 422.

A cutter 403 can be attached to the imaging shaft 422, such as through a connecting collar 433. The cutter 403 can include a fluted distal end 412 configured to bore through tissue. Further, the cutter 403 can include a mirror 499 affixed to the proximal end thereof at an angle, such as between 35 and 55 degrees, e.g., 45 degrees, relative to the central axis of the fiber 497.

The imaging shaft 422 can further include an imaging window 407 therein. The imaging window 407 can be placed in such a location as to allow the light deflected off of the mirror 499 to travel through the window 407 into adjacent tissue.

The imaging shaft 422 can be configured to rotate, thereby rotating the cutter 403, including the distal cutting edge 412 (to cut tissue) as well as the mirror 499. By rotating the mirror 499, the beam traveling through the fiber 497 will bounce off the mirror 499 and be sent into, and received back from, areas all around the circumference of the vessel in which the device 400 is placed.

Advantageously, by rotating the mirror 499 rather than the optical fiber 497, complicated fiber management mechanisms are eliminated. Moreover, the imaging shaft 422 can be rotated at high speeds, such as greater than 1,000 rpm, to provide better drilling with the cutting edge 412 as well as higher imaging rates, such as rates of greater than 10 frames per section (fps), such as greater than 10 fps, such as approximately 16.67 fps. In an exemplary embodiment, the rate of Laser sweep, such as approximately 20 KHz, can be configured to keep up with at 16.67 frames per second with about 1200 lines per frame. Furthermore, by having the fiber 497 extend through the center of the device 400, the device 400 can advantageously be less than 0.03" in diameter, such as less than 0.02" in diameter, such as approximately 0.018" in diameter. Accordingly, the device 400 can advantageously be used in small-diameter peripheral arteries and coronary arteries.

In some embodiments, referring to FIG. 4A, the device 400 can include an outer sheath 411 therearound. The outer sheath 411 can be stationary relative to the rotatable imaging shaft 422, thereby making it easier for a user to hold onto the device. In some embodiments, the outer sheath can be attached to the imaging shaft 422, such as through a bearing. In other embodiments, the outer sheath 411 can be unattached to the remainder of the device. In some embodiments, the outer sheath 411 can include a clear annular section similar to the annular section 121 described above with respect to FIGS. 1A-2B.

In some embodiments, the device 400 can further include a monorail guidewire lumen similar to the device 100 described above.

The device 400 can be attached to a drive system to provide a light source for OCT imaging and/or to provide torque for rotation of the imaging shaft.

In some embodiments, an occlusion-crossing device can include a deflectable tip configured to protect the distal tip when in use.

For example, referring to FIGS. 5A-5E, an occlusion-crossing device 500 can include a catheter body 501, a cutter 503, and a deflectable distal tip 505 at the distal end. The catheter body 501 can include an outer shaft 511 and an imaging shaft 513 extending therein. As described above with respect to devices 100 and 400, the device 500 can include an imaging element 492, such as an optical fiber extending through the imaging shaft 513 so as to run substantially along the central axis of the catheter body 501. A mirror 599 oriented at 35-55 degrees, such as 45 degrees, can be configured to project the light into the tissue at a 90 degree angle relative to the optical fiber. The cutter 503 can be attached to the imaging shaft 513. The cutter 503 can include a perforating tip 572 extending off of the distal end thereof. The perforating tip 572 can be configured to penetrate tissue as it is advanced and/or rotated. For example, the perforating tip 572 can be shaped as a fluted end mill or drill or a plurality of shape-set sharp whiskers. The perforating tip 472 can have a diameter that is smaller than the diameter of the rest of the cutter 503 and/or the elongate body 501, thereby advantageously providing a sharper or more pronounced point for drilling. The size of the perforating tip 572 can further be approximately the size of the guidewire 590, thereby helping to provide a hole through which the guidewire can extend.

Figure 5A:
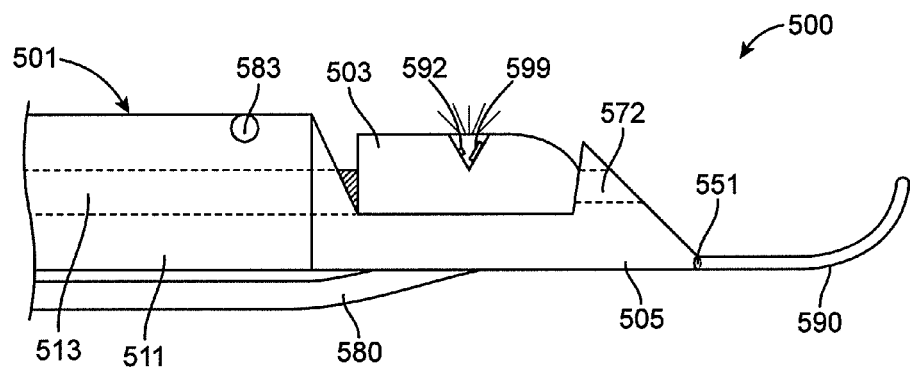
Figure 5B:
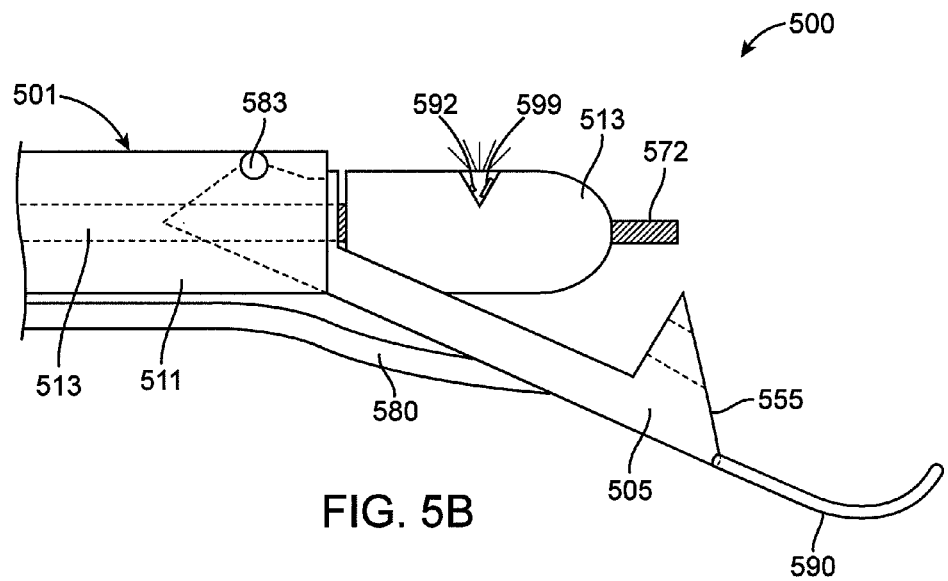

In some embodiments, a guidewire lumen 580, such as a monorail guidewire lumen 580 can run along the outside of the device to hold a guidewire 590. Further, in some embodiments, as shown in FIGS. 5A-5C, the guidewire lumen 580 can extend through the distal tip 505 and extend out of the distal-most end 551 of the distal tip 505.

The deflectable distal tip 505 can be attached to the outer shaft 511 at a hinge point 583, such as at a hinge pin. The deflectable distal tip 505 can have a wedged distal edge 555, best shown in FIGS. 5D-5E. The wedged distal edge 555 can advantageously be aligned with a hard or dense occlusion such that the distal-most end 551 of the distal tip 505 is oriented partially around the occlusion (along the side of the vessel). When the distal tip 505 is deflected, this position can be enhanced, allowing the guidewire lumen 550 and guidewire 590 to aim around the occlusion. Using a guidewire 590 having a curved distal end, as shown in FIG. 590, can help the guidewire slide along the occlusion even as the distal-most edge 551 of the tip 505 (and thus the guidewire lumen 580) is pointed towards the vessel wall.

Further, the deflectable distal tip can have a cut-out 587 configured to house the perforating tip 572 therein. The deflectable distal tip can be deflected, for example, by pulling or pushing on the drive shaft 513, similar to embodiments described in International Patent Application titled "BALLOON ATHERECTOMY CATHETERS WITH IMAGING," filed herewith; U.S. patent application Ser. No. 13/175,232, titled "ATHERECTOMY CATHETERS WITH LONGITUDINALLY DISPLACEABLE DRIVE SHAFTS," filed Jul. 1, 2011, Publication No. US-2012-0046679-A1; U.S. patent application Ser. No. 12/829,277, titled "ATHERECTOMY CATHETER WITH LATERALLY-DISPLACEABLE TIP," filed Jul. 1, 2010, Publication No. US-2011-0004107-A1; International Patent Application titled "ATHERECTOMY CATHETERS WITH IMAGING," all of which are incorporated by reference herein. The deflectable distal tip 505 can thus have a closed configuration, as shown in FIG. 5A, wherein the deflectable tip 505 covers the perforating tip 572, and an open configuration where the deflectable tip 505 exposes the perforating tip 572.

In some embodiments, the imaging shaft 513 can be moved proximally and distally. Distal extension of the imaging shaft 513 when the deflectable distal tip 505 is deflected can advantageously extend the perforating tip 572 past the distal end of the tip 505 to provide for drilling with the deflectable tip 572 out of the way.

Because the optical fiber runs through the center of the device, the imaging shaft 513 can advantageously be rotated at high speeds in a single direction, such as greater than 1,000 rpm, to provide better drilling with the cutting edge 412 as well as higher imaging rates, as described above with respect to devices 100 and 400. Furthermore, by having the fiber of the imaging sensor 592 extend through the center of the device 500, the device 500 can advantageously be less than 0.10", such as less than 0.08", such as less than 0.07", less than 0.06", or less than 0.05". Accordingly, the device 500 can advantageously be used in small-diameter peripheral arteries and coronary arteries.

In operation, the device 500 can be advanced through the vasculature with the tip 505 in the non-deflected position (shown in FIG. 5A). At the target lesion or CTO, the device 500 can continue to be advanced until an obstruction is encountered that cannot be passed by the device 500. At this point, the imaging sensor 592 can be used to identify structures in the vessel that could potentially be easier to pass through (non-ossified material). The device 500 can then be re-oriented the tip 505 deflected (as shown in FIG. 5C) to facilitate 'aiming' the guide wire lumen 580 in the direction of the more penetrable structure. The guide wire 590 can then be advanced along a new trajectory while being supported by the guide wire lumen 580. Once the guide wire 590 has traversed some distance through the obstacle, the tip 505 of the device can be returned to the normal (non-deflected) position to facilitate passage over the guide wire. If further obstacles are encountered, the process can be repeated until complete passage of the lesion or CTO had been achieved. In embodiments where the distal tip 503 includes a perforating tip 572, a hole can be created in the occlusion to help pass the guidewire therethrough.

Any of the catheters described herein can be shape-set or include shape-set features to enhance trackability and navigability.

As used herein, an imaging element can include the OCT optical fiber, such as the distal end of the optical fiber, as well as the mirror and adhesive used to hold the mirror and optical fiber in place.

As described above, the catheters described herein can include optical coherence tomography imaging, such as common path OCT. Such OCT systems are described in U.S. patent application Ser. No. 12/829,267, titled "CATHETER-BASED OFF-AXIS OPTICAL COHERENCE TOMOGRAPHY IMAGING SYSTEM," filed Jul. 1, 2010, Publication No. US-2010-0021926-A1; U.S. patent application Ser. No. 12/790,703, titled "OPTICAL COHERENCE TOMOGRAPHY FOR BIOLOGICAL IMAGING," filed May 28, 2010, Publication No. US-2010-0305452-A1; and International Patent Application titled "OPTICAL COHERENCE TOMOGRAPHY WITH GRADED INDEX FIBER FOR BIOLOGICAL IMAGING," filed herewith, all of which are incorporated by reference in their entireties. Alternatively, other types of imaging could be used with the catheters described herein. For example, the devices described herein could be configured to work with infrared spectroscopy or ultrasound.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. An imaging device comprising:
   a hollow flexible shaft having a central longitudinal axis and an imaging window therein;
   an outer sheath extending around the hollow flexible shaft, wherein the outer sheath includes an optically clear annular section at a distal end thereof;
   an optical fiber extending within the hollow flexible shaft substantially along the central axis, a distal tip of the optical fiber attached to the hollow flexible shaft and aligned with the imaging window so as to transfer an optical coherence tomography signal through the imaging window; and
   a handle attached to the hollow flexible shaft configured rotate the hollow flexible shaft at speeds of greater than 1,000 rpm.

2. The imaging device of claim 1, wherein the optical fiber extends substantially along the central axis for the entire length of the fiber.

3. The imaging device of claim 1, wherein the device is less than 0.1 inches in diameter.

4. The imaging device of claim 3, wherein the device is less than 0.08 inches in diameter.

5. The imaging device of claim 4, wherein the device is less than 0.05 inches in diameter.

6. The imaging device of claim 1, wherein the hollow flexible shaft is made of tungsten.

7. The imaging device of claim 1, wherein the hollow flexible shaft is made of multiple layers of wound filars.

8. The imaging device of claim 7, wherein the filars are counterwound.

9. The imaging device of claim 1, wherein the hollow flexible shaft further includes a mirror therein configured to reflect light from the optical fiber into adjacent tissue.

10. A method of imaging a body lumen, the method comprising:
    inserting an outer sheath into the body lumen, the outer sheath having an optically clear annular section at a distal end thereof;
    inserting an imaging device into a lumen of the other sheath, the imaging device including a hollow flexible shaft having a central longitudinal axis with an imaging window therein and an optical fiber extending within the hollow flexible shaft, wherein a distal tip of the optical fiber is attached to the hollow flexible shaft and aligned with the imaging window, the optical fiber extending substantially along the central longitudinal axis;
    rotating the hollow flexible shaft within the lumen of the outer sheath with a handle attached to the hollow flexible sheath at speeds greater than 1,000 rpm; and
    collecting images of the body lumen through the imaging window and the optically clear annular section with the optical fiber.

11. The method of claim 10, wherein collecting images of the body lumen comprises collecting images of the body lumen at rates of greater than 10 frames per minute.

12. The method of claim 10, wherein the body lumen is a coronary artery.

13. The method of claim 10, wherein the body lumen is a peripheral artery.

14. The method of claim 10, wherein the imaging device includes a cutter thereon, the method further comprising cutting tissue of the body lumen with the cutter to pass through an occlusion in the body lumen.

15. The method of claim 14, further comprising removing the imaging device from the lumen of the outer sheath and advancing a guidewire through the lumen of the outer sheath after passing the cutter through the occlusion.

* * * * *